United States Patent [19] [11] 4,183,932
Yamamoto et al. [45] Jan. 15, 1980

[54] FUSED QUINAZOLINONES AND PREPARATION THEREOF

[75] Inventors: Michihiro Yamamoto; Masao Koshiba, both of Nishinomiya; Hisao Yamamoto, Kobe, all of Japan

[73] Assignee: Sumitomo Chemical Company, Limited, Osaka, Japan

[21] Appl. No.: 873,785

[22] Filed: Jan. 31, 1978

[30] Foreign Application Priority Data

Feb. 9, 1977 [JP] Japan .................. 52-13818

[51] Int. Cl.[2] .................. A61K 31/41; C07D 487/04; C07D 487/14
[52] U.S. Cl. .................. 424/251; 544/247; 544/250; 544/251; 544/286; 544/292
[58] Field of Search .................. 544/247, 250, 251; 424/251

[56] References Cited

U.S. PATENT DOCUMENTS

| | | | |
|---|---|---|---|
| 4,002,755 | 1/1977 | Yamamoto et al. | 544/251 |
| 4,056,384 | 11/1977 | Bowie et al. | 544/251 |
| 4,085,212 | 4/1978 | Burrell et al. | 544/251 |
| 4,085,213 | 4/1978 | Bindra | 544/250 |
| 4,087,422 | 5/1978 | Bowie | 544/251 |

OTHER PUBLICATIONS

Bogatskii, et al., "Chemical Abstracts," Vol. 88, 1978, col. 6829r.

Primary Examiner—Donald G. Daus
Assistant Examiner—James H. Turnipseed
Attorney, Agent, or Firm—Stevens, Davis, Miller & Mosher

[57] ABSTRACT

Tricyclic quinazolines of the formula,

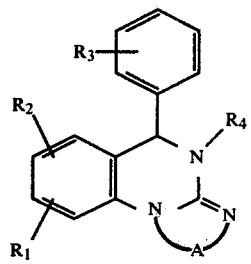

wherein $R_1$, $R_2$, $R_3$, $R_4$ and A are as defined in the specification, such as 4,5-dihydro-5-arylimidazo[1,2-a]quinazolines, 4,5-dihydro-5-aryl-s-triazolo[4,3-a]quinazolines and 4,5-dihydro-5-aryltetrazolo[1,5-a]quinazolines having anti-inflammatory and analgesic activity are, for example, prepared by reducing the corresponding 4,5-unsaturated compounds, and then, if necessary, by alkylating the thus produced compounds.

3 Claims, No Drawings

FUSED QUINAZOLINONES AND PREPARATION THEREOF

This invention relates to novel tricyclic quinazolines and processes for preparation thereof.

More particularly, the present invention pertains to tricyclic quinazolines of the formula,

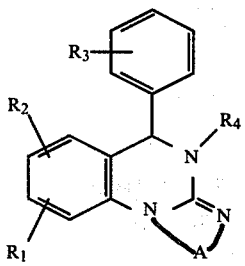

(I)

wherein $R_1$, $R_2$ and $R_3$ are independently hydrogen, halogen, $C_{1-4}$ alkyl, $C_{1-4}$ alkoxy or nitro, and further $R_1$ and $R_2$ may together represent methylenedioxy; $R_4$ is hydrogen or $C_{1-4}$ alkyl; and A is a double bond selected from the group consisting of C=C, C=N and N=N (wherein the carbon atom may optionally bear a $C_{1-4}$ alkyl radical), and pharmaceutically acceptable acid addition salts thereof.

In the compounds of the above formula (I) and elsewhere in the specification, the term "alkyl" means both straight- and branched-chain saturated aliphatic hydrocarbon radicals, and the $C_{1-4}$ alkyl may be methyl, ethyl, n-propyl, isopropyl, n-butyl or isobutyl; the $C_{1-4}$ alkoxy may be methoxy, ethoxy, n-propoxy, isopropoxy, n-butoxy or isobutoxy; and the term "halogen" includes fluorine, chlorine, bromine or iodine.

It is an object of the present invention to provide novel tricyclic quinazoline derivatives of the formula (I) having pharmacological activity. It is a further object of the present invention to provide processes for preparing the same.

This invention also includes addition salts of the compounds of the formula (I) formed with pharmaceutically acceptable acids. Such acids include both organic and inorganic acids, for example: acetic, propionic, tartaric, citric, maleic, fumaric, ascorbic, oxalic, succinic, gluconic, glycolic, lactic, malic, mandelic, salicylic, glutamic, aspartic, stearic, palmitic, hydrochloric, hydrobromic, hydroiodic, sulfuric and phosphoric acids.

Tricyclic quinazoline derivatives of the formula (I) have prominent pharmacological properties, particularly anti-inflammatory and analgesic activity. For example, 7-chloro-4,5-dihydro-4-methyl-5-phenyl-triazolo[1,5-a]quinazoline shows remarkable inhibitory action for carrageenin-induced edema in rats at doses as low as 100 mg/kg orally, while no toxic symptoms are observed.

The compounds of the present invention may be administered enterally or parenterally in therapeutic dosage forms with dosage adjusted to individual needs, that is, in solid or liquid dosage forms such as tablets, dragees, capsules, suspensions, solutions, elixirs and the like.

According to the present invention tricyclic quinazoline derivatives of the formula (I) may be prepared by the following methods.

One method for synthesis of the compounds of the formula (I), comprises reacting a compound of the formula,

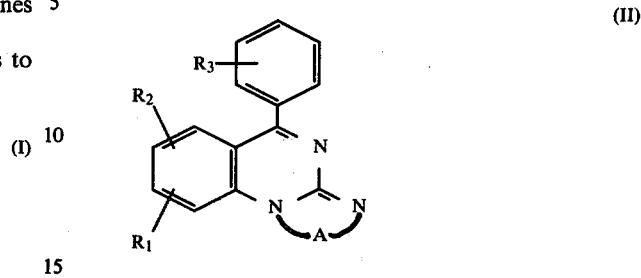

(II)

wherein $R_1$, $R_2$, $R_3$ and A are as defined above, with a reducing agent to give a compound of the formula,

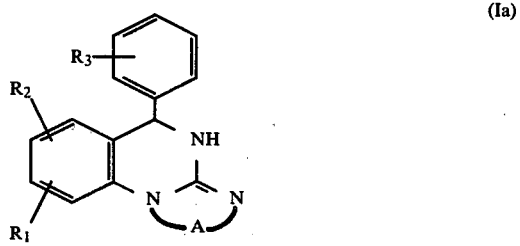

(Ia)

wherein $R_1$, $R_2$, $R_3$ and A are as defined above, and then, if necessary, reacting the so produced compound with an alkylating agent.

The suitable reducing agents are, for example, complex metal hydrides such as sodium borohydride, lithium borohydride, lithium aluminum hydride, diisobutylaluminum hydride, sodium aluminum diethyl hydride and sodium bis(2-methoxyethoxy)aluminum hydride, and hydrogen together with a metal catalyst such as nickel, palladium, platinum oxide, copper or cobalt. The reaction may be effected in the presence of an inert organic solvent such as methanol, ethanol, isopropanol, diethyl ether, tetrahydrofuran, dioxane, dimethylformamide, benzene or toluene. The temperature is not critical and may be varied from about 0° to about 100° C.

The alkylation of a compound of the formula (Ia) is preferably carried out in the presence of an inert solvent and a basic condensing agent with an alkylating agent having a $C_{1-4}$ alkyl moiety. Suitable alkylating agents are an alkyl halide, e.g. alkyl chloride, alkyl bromide or alkyl iodide, an alkyl sulfonate, e.g. alkyl paratoluene sulfonate, alkyl benzene sulfonate or alkyl methane sulfonate, and an alkyl sulfate, e.g. dimethyl sulfate or diethyl sulfate. Suitable condensing agents include sodium hydride, sodium amide, sodium methoxide, sodium hydroxide, potassium carbonate and the like. Of these, sodium hydride is preferred. Solvents that may be used include benzene, toluene, xylene, dimethylformamide, dimethylacetamide, tetrahydrofuran, dioxane, acetone, dimethylsulfoxide and the like. The temperature and duration of the reaction are not critical and may be varied, e.g. temperatures from room temperature to the boiling point of the solvent employed, and the duration from 1 to about 10 hours.

A further method for synthesis of the tricyclic quinazoline derivatives of the formula,

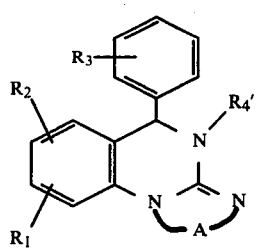

(Ib)

wherein $R_1$, $R_2$, $R_3$ and A are as defined above; and $R_4'$ is $C_{1-4}$ alkyl, comprises cyclizing a compound of the formula,

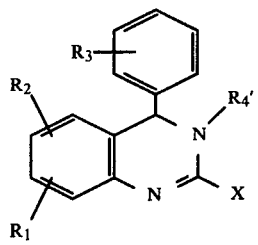

(III)

wherein $R_1$, $R_2$, $R_3$ and $R_4'$ are as defined above; and X is 2,2-di-$C_{1-4}$alkoxyethylamino, $C_{1-5}$acylhydrazino or azido, with heating.

The above-mentioned process will be explained in detail hereinafter for the preparation of individual compounds of the formula (Ib) depending upon three types of structures in the definition of A.

The compounds of the formula,

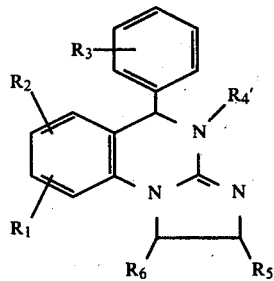

(Ic)

wherein $R_1$, $R_2$, $R_3$ and $R_4'$ are as defined above; and $R_5$ and $R_6$ are each hydrogen or $C_{1-4}$ alkyl but which cannot be $C_{1-4}$ alkyl at the same time, are prepared by reacting a quinazoline derivative of the formula,

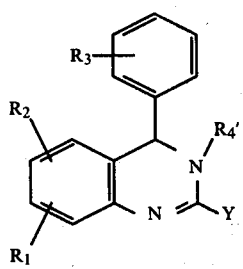

(IV)

wherein $R_1$, $R_2$, $R_3$ and $R_4'$ are as defined above; and Y is halogen or methylthio, with an amine of the formula

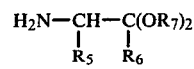

(V)

wherein $R_5$ and $R_6$ are as defined above; and $R_7$ is $C_{1-4}$ alkyl, to give a compound of the formula,

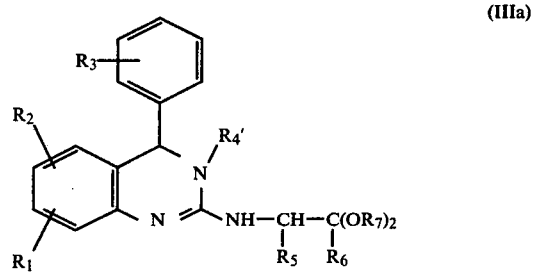

(IIIa)

wherein $R_1$, $R_2$, $R_3$, $R_4'$, $R_5$, $R_6$ and $R_7$ are as defined above, and then cyclizing the so produced compound with heating in the presence of an acid.

Suitable acids which may be employed in this reaction include sulfuric acid, hydrochloric acid, polyphosphoric acid, acetic acid and the like. If desired, the reaction may be carried out in the presence of a suitable inert organic solvent. However, the use of a solvent is not necessary since an excess of both the amine and the acid can be used for this purpose in the corresponding reaction step.

The compounds of the formula,

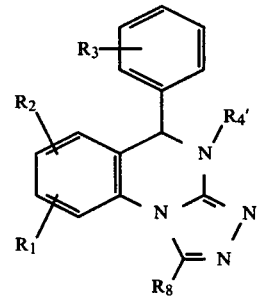

(Id)

wherein $R_1$, $R_2$, $R_3$ and $R_4'$ are as defined above; and $R_8$ is $C_{1-4}$ alky, are prepared by either reacting the compound of the aforesaid formula (IV) with an acylhydrazine of the formula,

$R_8$—CONHNH$_2$ (VI)

wherein $R_8$ is as defined above, or reacting a hydrazinoquinazoline of the formula,

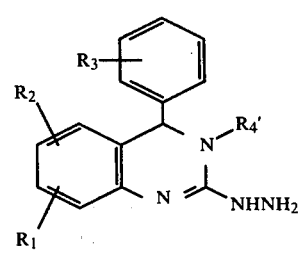

(VII)

wherein R₁, R₂, R₃ and R₄' are as defined above, with a carboxylic acid of the formula,

R₈—COOH     (VIII)

wherein R₈ is as defined above, or its reactive derivative, to give a compound of the formula,

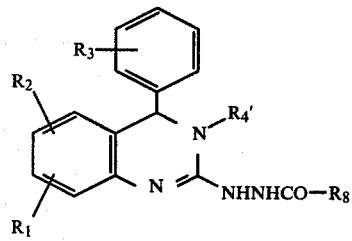

(IIIb)

wherein R₁, R₂, R₃, R₄' and R₈ are as defined above, and then cyclizing the so produced compound with heating.

Examples of the reactive derivative of the carboxylic acid of the formula (VIII) include acid anhydrides, acid halides, acid esters and orthoesters of the formula R₈—C(OR₉)₃ wherein R₉ is $C_{1-4}$ alkyl. The cyclization may be carried out at elevated temperatures of up to about 250° C. in the presence or absence of an inert solvent and a condensing agent. Suitable solvents are, for example, benzene, toluene, xylene, chlorobenzene, nitrobenzene, ethanol, propanol, butanol, methoxyethanol, ethoxyethanol, dimethoxyethane, pyridine, dimethylformamide and dimethylsulfoxide. The condensing agents which may be employed in this process are, for example, sulfuric acid, phosphoric acid, polyphosphoric acid, hydrochloric acid, acetic acid, methanesulfonic acid and toluenesulfonic acid.

The compounds of the formula,

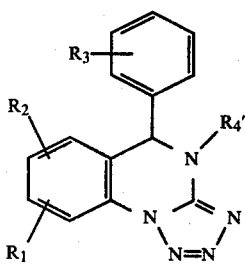

(Ie)

wherein R₁, R₂, R₃ and R₄' are as defined above, are prepared by either reacting the compound of the aforesaid formula (IV) with an azide in an inert solvent, or reacting the hydrazinoquinazoline derivative of the aforesaid formula (VII) with sodium nitrite in an aqueous acid solution, via a compound of the formula,

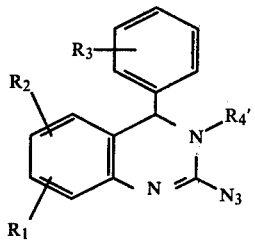

(IIIc)

wherein R₁, R₂, R₃ and R₄' are as defined above. Suitable solvents for the reaction of the compound of the formula (IV) with an azide are, for example, dimethylsulfoxide, dimethylformamide or dimethylacetamide. The preferred azides are, for example, sodium azide, lithium azide and diphenylphosphorylazide. The cyclization of the intermediate of the formula (IIIc) may be effected at elevated temperatures of up to about 200° C.

According to the processes of the present invention, there are obtained, for example, the following tricyclic quinazoline derivatives.

7-Chloro-4,5-dihydro-5-phenylimidazo[1,2-a]quinazoline.

7-Chloro-4,5-dihydro-4-methyl-5-phenylimidazo[1,2-a]quinazoline.

7-Chloro-4,5-dihydro-1-methyl-5-phenylimidazo[1,2-a]quinazoline.

4,5-Dihydro-4-ethyl-7-methoxy-5-phenylimidazo[1,2-a]quinazoline.

4,5-Dihydro-7,8-methylenedioxy-5-phenylimidazo[1,2-a]quinazoline.

7-Chloro-4,5-dihydro-5-phenyl-s-triazolo[4,3-a]quinazoline.

7-Chloro-4,5-dihydro-1-methyl-5-phenyl-s-triazolo[4,3-a]quinazoline.

4,5-Dihydro-4,8-dimethyl-5-phenyl-s-triazolo[4,3-a]quinazoline.

4,5-Dihydro-4-methyl-7-nitro-5-phenyl-s-triazolo[4,3-a]quinazoline.

7-Chloro-4,5-dihydro-4-methyl-5-phenyl-s-triazolo[4,3-a]quinazoline.

4,5-Dihydro-5-phenyltetrazolo[1,5-a]quinazoline.

8-Chloro-4,5-dihydro-5-phenyltetrazolo[1,5-a]quinazoline.

7-Chloro-4,5-dihydro-4-methyl-5-phenyltetrazolo[1,5-a]quinazoline.

7,8-Dihydro-4,5-dihydro-5-phenyltetrazolo[1,5-a]quinazoline.

7-Chloro-4,5-dihydro-5-(o-fluorophenyl)tetrazolo[1,5-a]quinazoline.

7-Chloro-4,5-dihydro-5-(p-chlorophenyl)tetrazolo[1,5-a]quinazoline.

4-n-Butyl-7-chloro-4,5-dihydro-5-phenyltetrazolo[1,5-a]quinazoline.

The following examples are given to illustrate the present invention more precisely, but they should not be interpreted to restrict the present invention thereto.

EXAMPLE 1

To a suspension of 1.3 g of 7-chloro-5-phenyltetrazolo[1,5-a]quinazoline in 100 ml of ethanol was added 0.2 g of sodium borohydride. The mixture was stirred at room temperature for 1 hour and then poured into 200 ml of water. The resulting precipitate was collected by filtration, washed with water and recrystallized from methanol to give 0.98 g of 7-chloro-4,5-dihydro-5- phenyltetrazolo[1,5-a]quinazoline as colorless needles, m.p. 260°–261° C. (decomp.).

The starting material may be prepared as follows: To a solution of 1.92 g of 2,6-dichloro-4-phenylquinazoline in 30 ml of dimethylsulfoxide was added 0.91 g of sodium azide. The mixture was heated at 100° C. for 1 hour with stirring and then poured into ice-water. The resulting precipitate was collected by filtration, washed with water and dried to give 1.9 g of 7-chloro-5-phenyltetrazolo[1,5-a]quinazoline. Recrystallization from chloroform-ethanol gave pale yellow needles, m.p. 209° C. (decomp.).

EXAMPLE 2

According to substantially the same procedures as that of Example 1, the following compounds were obtained from the corresponding starting compounds.

4,5-Dihydro-7-methoxy-5-phenyltetrazolo[1,5-a]quinazoline, m.p. 241° C. (decomp.).

4,5-Dihydro-5-phenyltetrazolo[1,5-a]quinazoline, m.p. 247° C. (decomp.).

8-Chloro-4,5-dihydro-5-phenyltetrazolo[1,5-a]quinazoline, m.p. 212° C. (decomp.).

4,5-Dihydro-7,8-methylenedioxy-5-phenyltetrazolo[1,5-a]quinazoline, m.p. 250° C. (decomp.).

7-Chloro-4,5-dihydro-5-(o-methylphenyl)tetrazolo[1,5-a]quinazoline, m.p. 300° C. (decomp.).

7-Chloro-4,5-dihydro-5-(m-chlorophenyl)tetrazolo[1,5-a]quinazoline, m.p. 269.5° C. (decomp.).

4,5-Dihydro-8-nitro-5-phenyltetrazolo[1,5-a]quinazoline, m.p. 252° C. (decomp.).

EXAMPLE 3

To a suspension of 0.4 g of 7-chloro-4,5-dihydro-5-phenyltetrazolo[1,5-a]quinazoline in 20 ml of dimethylformamide was added 0.07 g of 50% sodium hydride. After the mixture was stirred at room temperature for 1 hour, 0.4 g of methyl iodide was added thereto. The resulting mixture was stirred at room temperature for 2 hours and then poured into ice-water. The mixture was stirred with a small quantity of isopropyl ether, and the resulting precipitate was collected by filtration, washed successively with water and isopropyl ether, and dried to give 0.26 g of 7-chloro-4,5-dihydro-4-methyl-5-phenyltetrazolo[1,5-a]quinazoline as pale yellow crystals. Recrystallization from ethanol gave colorless scales, m.p. 282°–283° C.

EXAMPLE 4

According to substantially the same procedures as that of Example 3, the following compounds were obtained from the corresponding starting compounds.

7-Chloro-4,5-dihydro-4-ethyl-5-phenyltetrazolo[1,5a]quinazoline, m.p. 117° C.

7-Chloro-4,5-dihydro-5-phenyl-4-(n-propyl)tetrazolo[1,5-a]quinazoline, m.p. 157°–157.5° C.

EXAMPLE 5

To a suspension of 2.6 g of 7-chloro-5-phenyl-s-triazolo[4,3-a]quinazoline in 100 ml of dimethylformamide was added 1 g of sodium borohydride. The mixture was stirred at room temperature overnight and then poured into ice-water. The resulting precipitate was collected by filtration, washed with water and dried. The so obtained solid was suspended in a mixture of 30 ml of methanol and 30 ml of concentrated hydrochloric acid, and the mixture was heated under reflux for 40 minutes. After cooling, the resulting mixture was neutralized with ammonia water. The precipitate formed was collected by filtration, washed with water, and recrystallized from methanol to give 1.2 g of 7-chloro-4,5-dihydro-5-phenyl-s-triazolo[4,3-a]quinazoline as colorless prisms, m.p. 241.5°–243.5° C.

The starting material may be prepared according to the methods which are described in U.S. Pat. No. 4,002,755.

EXAMPLE 6

To a suspension of 1.3 g of 7-chloro-1-methyl-5-phenyl-s-triazolo[4,3-a]quinazoline in 70 ml of dimethylformamide was added 0.5 g of sodium borohydride. The mixture was heated with stirring at 75°–80° C. for 2 hours and then poured into ice-water. The resulting mixture was neutralized with dilute hydrochloric acid, and the precipitate formed was collected by filtration and washed with water. The solid was then suspended in a mixture of 40 ml of methanol and 5 ml of concentrated hydrochloric acid, and the mixture was stirred at room temperature for 2 hours. After neutralization with ammonia water, the mixture was extracted with chloroform. The chloroform layer was dried over anhydrous sodium sulfate, and the solvent was removed under reduced pressure. The residue was recrystallized from dimethylformamideethanol to give 0.75 g of 7-chloro-4,5-dihydro-1-methyl-5-phenyl-s-triazolo[4,3-a]quinazoline as colorless needles, m.p. 262°–265° C.

EXAMPLE 7

According to substantially the same procedure as that of Example 6, there was obtained the following compound from the corresponding starting compound.

7-Chloro-4,5-dihydro-1-ethyl-5-phenyl-s-triazolo[4,3-a]quinazoline, m.p. 231.5°–232.5° C.

EXAMPLE 8

To a suspension of 0.28 g of 7-chloro-5-phenylimidazo[1,2-a]quinazoline in 20 ml of ethanol was added 0.2 g of sodium borohydride, and the mixture was heated under reflux for 10 hours. After cooling, the mixture was poured into ice-water, and the resulting precipitate was collected by filtration, washed with water and dried. The product was dissolved in chloroform and absorbed on an activated alumina column. Elution with chloroform and recrystallization from ethanol gave 7-chloro-4,5-dihydro-5-phenylimidazo[1,2-a]quinazoline (m.p. 239°–241° C.) and 7-chloro-1,2,4,5-tetrahydro-5-phenylimidazo[1,2-a]quinazoline (m.p. 210°–213° C.).

The starting material may be prepared as follows: To a suspension of 5.5 g of 2,6-dichloro-4-phenylquinazoline in 70 ml of dimethylsulfoxide was added 4.2 g of 2,2-dimethoxyethylamine. The mixture was heated at 90°–100° C. for 1.5 hours with stirring. After cooling, the mixture was poured into 400 ml of ice-water. The resulting mixture was stirred with a small quantity of n-hexane, and the precipitate that formed was collected by filtration, washed with water and dried to give 6.9 g of 6-chloro-2-(2,2-dimethoxyethylamino)-4-phenylquinazoline. Recrystallization from ethanol gave yellow needles, m.p. 122.5°–123° C.

A mixture of 1.72 g of the so obtained quinazoline and 20 ml of concentrated sulfuric acid was heated at 100° C. for 25 minutes. After cooling, the mixture was poured onto ice, and the resulting mixture was neutralized with 30% sodium hydroxide solution. The mixture was then extracted with chloroform, and the chloroform layer was washed with water, dried over anhydrous sodium sulfate and evaporated under reduced pressure to give 1.5 g of 7-chloro-5-phenylimidazo[1,2-a]quinazoline. Recrystallization from dimethylformamide gave light yellow needles, m.p. 270.5°–271.5° C.

EXAMPLE 9

To a suspension of 1.38 g of 7-methoxy-5-phenylimidazo[1,2-a]quinazoline in 25 ml of tetrahydrofuran was added 0.38 g of lithium aluminum hydride, and the mixture was stirred at room temperature for 3 hours. To the reaction mixture was added dropwise 1 ml of water with ice-cooling, and the resulting precipitate was filtered off and washed with tetrahydrofuran. The filtrate was evaporated under reduced pressure and the residue was recrystallized from ethylacetate-isopropyl ether to give 1.1 g of 4,5-dihydro-7-methoxy-5-phenylimidazo[1,2-a]quinazoline, m.p. 178°–179° C. (decomp.).

EXAMPLE 10

According to substantially the same procedure as that of Example 9, there was obtained the following compound from the corresponding starting compound.
4,5-Dihydro-7,8-methylenedioxy-5-phenylimidazo[1,2-a]quinazoline, m.p. 216°–217° C. (decomp.).

EXAMPLE 11

A mixture of 3.5 g of 6-chloro-3,4-dihydro-2-(2,2-dimethoxyethylamino)-3-methyl-4-phenylquinazoline and 20 ml of concentrated sulfuric acid was heated at 50°–60° C. for 2 hours. The reaction mixture was poured onto ice, and the resulting mixture was neutralized with concentrated ammonia water and then extracted with chloroform. The chloroform layer was washed with water, dried over anhydrous sodium sulfate, and concentrated to dryness. The residue was chromatographed on silica gel using chloroform as an eluent to give 1.1 g of 7-chloro-4,5-dihydro-4-methyl-5-phenylimidazo[1,2-a]quinazoline as viscid oil.

The starting material may be prepared as follows: A mixture of 3.0 g of 2,6-dichloro-3,4-dihydro-3-methyl-4-phenylquinazoline and 15 ml of 2,2-dimethoxyethylamine was heated at 100°–110° C. for 1 hour. The mixture was poured into ice-water and the resulting mixture was extracted with ether. The ether layer was washed with water, dried over anhydrous sodium sulfate, and concentrated to dryness. The residual oil was crystallized from isopropyl ether-hexane to give 2.0 g of 6-chloro-3,4-dihydro-2-(2,2-dimethoxyethylamino)-3-methyl-4-phenylquinazoline as colorless needles, m.p. 104.5°–105° C.

EXAMPLE 12

To a solution of 2.33 g of 2,6-dichloro-3,4-dihydro-3-methyl-4-phenylquinazoline in 30 ml of dimethylsulfoxide was added 1.0 g of sodium azide. The mixture was heated at 100° C. for 3 hours and then poured into ice-water. The precipitate formed was collected by filtration, washed with water and dried to give 2.3 g of 7-chloro-4,5-dihydro-4-methyl-5-phenyltetrazolo[1,5-a]quinazoline, m.p. 280° C.

What is claimed is:

1. A compound of the formula,

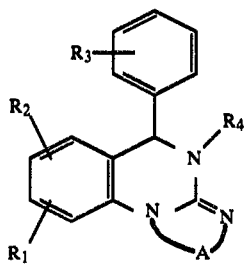

(I)

wherein $R_1$, $R_2$ and $R_3$ are independently hydrogen, halogen, $C_{1-4}$ alkyl, $C_{1-4}$ alkoxy or nitro, and further $R_1$ and $R_2$ may together represent methylenedioxy; $R_4$ is hydrogen or $C_{1-4}$ alkyl; and A is N=N and a pharmaceutically acceptable acid addition salt thereof.

2. A compound according to claim 1, which is represented by the formula,

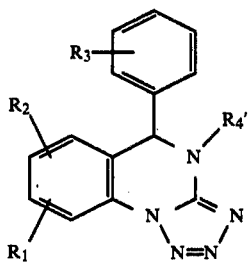

(Ie)

wherein $R_1$, $R_2$, $R_3$ are as defined in claim 1, and $R_4'$ is $C_1$–$C_4$ alkyl.

3. A pharmaceutical composition containing as an active ingredient one or more compounds of the formula (I) or pharmaceutically acceptable acid addition salts thereof, which is given and defined in claim 1, and a pharmaceutically acceptable diluent or carrier.

* * * * *